(12) United States Patent
Paulus et al.

(10) Patent No.: US 10,983,070 B2
(45) Date of Patent: Apr. 20, 2021

(54) METHOD FOR CHARACTERIZING AN OBJECT USING SPECTRAL IMAGING

(71) Applicant: Commissariat a l'energie atomique et aux energies alternatives, Paris (FR)

(72) Inventors: Caroline Paulus, Grenoble (FR); Andrea Brambilla, Grenoble (FR); Veronique Rebuffel, Grenoble (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 75 days.

(21) Appl. No.: 16/448,227

(22) Filed: Jun. 21, 2019

(65) Prior Publication Data

US 2019/0391090 A1     Dec. 26, 2019

(30) Foreign Application Priority Data

Jun. 22, 2018   (FR) .................................... 18 55616

(51) Int. Cl.
*G01N 23/04*     (2018.01)
*G01N 23/087*    (2018.01)

(52) U.S. Cl.
CPC ........... *G01N 23/04* (2013.01); *G01N 23/087* (2013.01); *G01N 2223/423* (2013.01)

(58) Field of Classification Search
CPC combination set(s) only.
See application file for complete search history.

(56) References Cited

U.S. PATENT DOCUMENTS 8,300,911 B1 * 10/2012 Payne ................... A61B 6/505
                                                           382/128
9,476,923 B2 * 10/2016 Beldjoudi .............. G01R 23/18

(Continued)

FOREIGN PATENT DOCUMENTS

EP    3 106 864 A1    12/2016
GB    2 454 782        5/2009
(Continued)

OTHER PUBLICATIONS

French Preliminary Search Report dated Jun. 5, 2019 in French Application 18 55616, filed on Jun. 22, 2018 (with English translation of categories of cited documents & Written Opinion).

(Continued)

*Primary Examiner* — Tsung Yin Tsai
(74) *Attorney, Agent, or Firm* — Oblon, McClelland, Maier & Neustadt, L.L.P.

(57) ABSTRACT

The invention is a method for characterizing an object (20), comprising the following steps:
  a) placing the object between a radiation source (10) and a radiation detector (30);
  b) irradiating the object with the radiation source and detecting radiation transmitted by the object (14) using the radiation detector, the radiation detector defining a plurality of pixels;
  c) for each pixel ($30_i$), forming an energy spectrum ($S_i$) of the detected radiation, each spectrum comprising at least two distinct energy bands;
  d) from each spectrum formed in c), estimating, in each pixel, at least two equivalent thicknesses ($\hat{L}_{i,1} \ldots \hat{L}_{i,M}, \hat{L}'_{i,1} \ldots \hat{L}'_{i,M}$) respectively associated with at least two basic materials ($mat_1 \ldots mat_M, mat'_1 \ldots mat'_M$);
wherein the method comprises, following d), the following steps:
  e) from the equivalent thicknesses resulting from d), calculating a structural parameter ($P_i$) of the object in various pixels ($30_i$);
  f) spatially smoothing the structural parameter calculated in a plurality of pixels;
  g) from the structural parameter smoothed in each pixel, and from each spectrum formed in c), estimating, in each pixel, regularized equivalent thicknesses ($\hat{L}_{i,m=1}|P_i^* \ldots \hat{L}_{i,m=M}|P_i^*, \hat{L}'_{i,m=1}|P_i^* \ldots \hat{L}'_{i,m=M}|P_i^*$).

10 Claims, 7 Drawing Sheets

(56) References Cited

U.S. PATENT DOCUMENTS

| | | | |
|---|---|---|---|
| 9,885,674 B2* | 2/2018 | Ouvrier-Buffet | G01T 1/171 |
| 10,371,651 B2* | 8/2019 | Barbes | G01N 23/2076 |
| 10,386,508 B2* | 8/2019 | Tabary | G01N 23/20091 |
| 2006/0074288 A1* | 4/2006 | Kelly | A61B 5/4869 |
| | | | 600/407 |
| 2009/0129544 A1* | 5/2009 | Chen | G01N 23/087 |
| | | | 378/62 |
| 2011/0235886 A1* | 9/2011 | Kelly | A61B 6/5294 |
| | | | 382/132 |
| 2013/0110438 A1* | 5/2013 | Rinkel | G06F 17/18 |
| | | | 702/85 |
| 2014/0270440 A1* | 9/2014 | Inglese | A61B 6/5205 |
| | | | 382/131 |
| 2014/0371570 A1* | 12/2014 | Davis | A61B 6/469 |
| | | | 600/407 |
| 2015/0285925 A1* | 10/2015 | Popa | G01T 7/005 |
| | | | 702/86 |
| 2016/0363442 A1* | 12/2016 | Brambilla | G01B 15/02 |
| 2016/0363545 A1 | 12/2016 | Gorecki et al. | |
| 2017/0125133 A1* | 5/2017 | Marticke | G01N 23/087 |

FOREIGN PATENT DOCUMENTS

| | | |
|---|---|---|
| WO | WO 2015/091083 A1 | 6/2015 |
| WO | WO 2017/211625 A1 | 12/2017 |

OTHER PUBLICATIONS

Alvarez, R., "Near optimal energy selective x-ray imaging system performance with simple detectors", Medical Physics, vol. 37, No. 2, 2010, pp. 822-841.

* cited by examiner

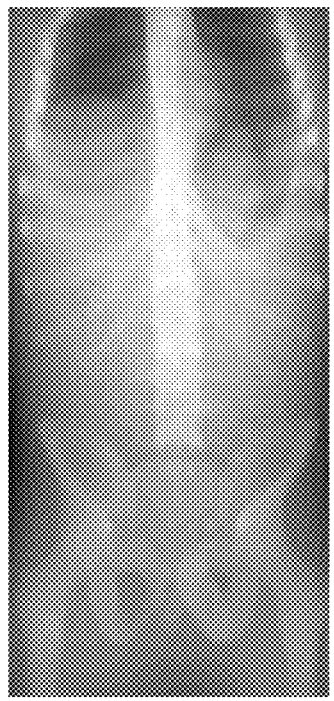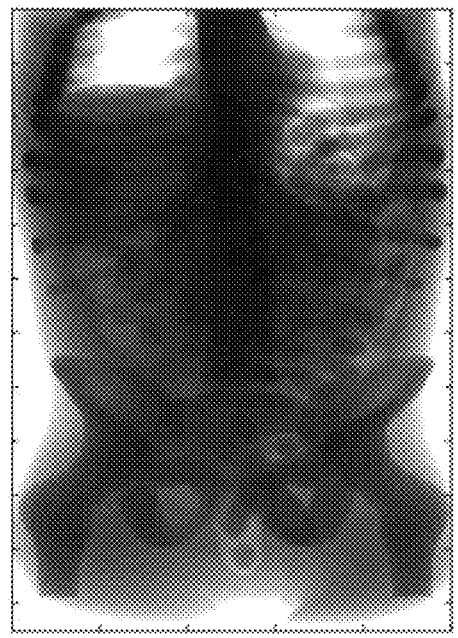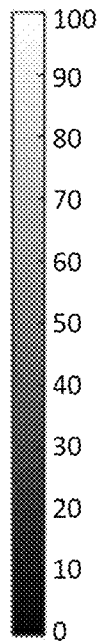
Fig. 3A
Fig. 3B
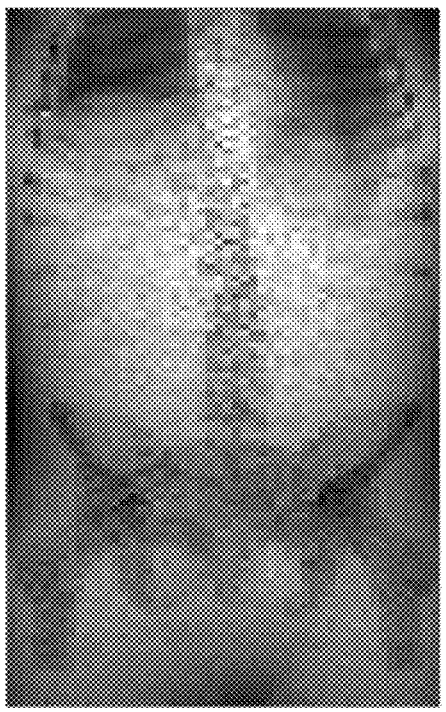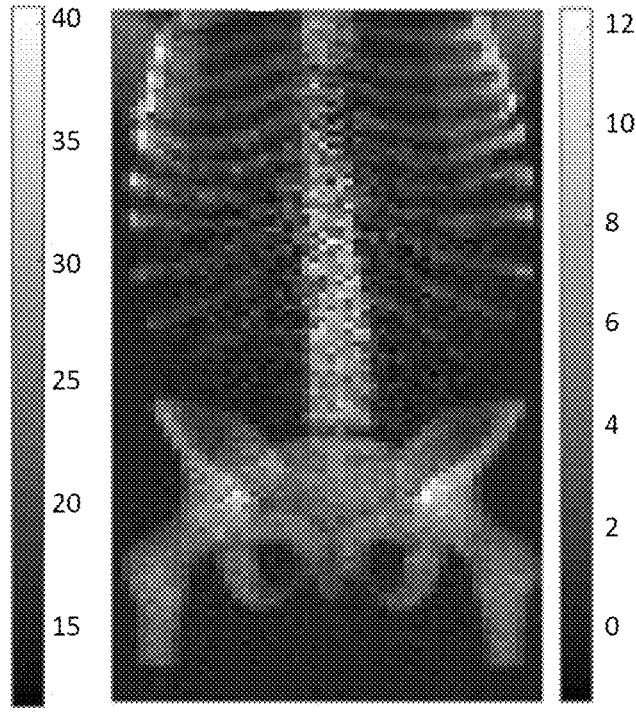
Fig. 3C
Fig. 3D

METHOD FOR CHARACTERIZING AN OBJECT USING SPECTRAL IMAGING

TECHNICAL FIELD

The technical field of the invention is the characterization of an object by irradiation using a source of x-rays or gamma radiation and the formation of a spectral image from radiation transmitted by the object.

PRIOR ART

The characterization of objects by irradiation using ionizing electromagnetic radiation, for example x-ray or gamma radiation, allows the nature of the materials from which this object is composed to be estimated. It is common to form an image representative of the attenuation of the radiation by the object. This image allows a two-dimensional characterization to be carried out.

Such a characterization may be carried out for the purposes of medical diagnosis, nondestructive testing in the industrial field, or even the detection of dangerous or illicit materials, for example in walk-through security scanners, such as those found in airports, or in the inspection of luggage.

The emergence of spatially and spectrally resolved detectors has allowed the performance of these characterizations to be substantially improved. This type of detector allows a spectral image of the attenuation of the analyzed object to be formed. By spectral image, what is meant is an image in various energy channels. A spectral image comprises various pixels. With each pixel is associated a spectrum of the radiation detected by the detector. This spectrum comprises a plurality of channels, each channel being representative of one energy band. Such a spectrum may comprise tens or even hundreds of channels.

The publication Alvarez R "Near optimal energy selective x-ray imaging system performance with simple detectors", Med. Phys. 37 (2), February 2010 describes a characterization of an object by formation of a spectrum representing an attenuation of ionizing radiation by the object. This publication describes a linear decomposition of the attenuation, in a basis composed of the attenuation of known materials. By attenuation of an object, what is meant is the attenuation, of radiation such as defined above, by the object. For example, when an object 20 to be characterized is provided, the spectral attenuation function $att_{20}$ of the analysed object may be approximated by a linear combination of spectral attenuation functions of known materials mat1 and mat2 according to the following expression:

$$att_{20} \approx L_1\mu_1 + L_2\mu_2 \tag{1}$$

where:
$att_{20}$ is the spectral attenuation of the examined object. The term "spectral" designates the fact that it is a question of a function defined at various energies E. The attenuation is proportional to the logarithm of the spectrum S of the radiation, attenuated by the object, and detected by the detector, according to the expression $att_{20} \propto -\ln(S)$ where $\propto$ designates proportionality.

$\mu_1$ and $\mu_2$ are respectively the linear attenuation spectral functions of the first material and of the second material. By linear attenuation, what is meant is an attenuation per unit length.

$L_1$ and $L_2$ are thicknesses, called equivalent thicknesses, of the first material mat1 and of the second material mat2.

$\approx$ means "being approximated by".

The spectral attenuation of the object $att_{20}$ is obtained from the spectrum of the radiation detected by the detector, $$att_{20} \approx -\ln\left(\frac{S}{S_0}\right),$$

$S_0$ being a spectrum of the radiation detected by the detector in the absence of object placed between the radiation source and the detector.

From the measurement of the spectrum S, the object may be characterized by an estimation of the equivalent thicknesses $L_1$ and $L_2$. The advantage of this is that spectral information on the attenuation of an object is obtained in at least two energy channels, allowing the equivalent thicknesses $L_1$ and $L_2$ to be determined. To do so, the attenuation $att_{20}$ of the object must be measured in at least two energy channels. Document EP3106864 proposes a method for estimating the equivalent thicknesses $L_1$ and $L_2$, this method being based on an approach of maximum-likelihood type.

By forming a spectral image of the object, i.e. a spatial distribution of spectra of the radiation attenuated by the object, it is possible to obtain equivalent thicknesses with various pixels, each pixel corresponding to one portion of the object.

The inventors desired to improve the existing methods by allowing an object to be characterized via a determination of equivalent thicknesses while requiring a lesser irradiation of the examined object.

SUMMARY OF THE INVENTION

A first subject of the invention is a method for characterizing an object, comprising the following steps:
 a) placing the object between a radiation source and a radiation detector, the radiation source being configured to emit ionizing electromagnetic radiation that propagates to the object;
 b) irradiating the object with the radiation source and detecting radiation transmitted by the object using the radiation detector, the radiation detector comprising a plurality of pixels, each pixel being associated with one portion of the object;
 c) for each pixel, forming an energy spectrum of the detected radiation, each spectrum comprising at least two distinct energy bands;
 d) from each spectrum formed in step c), estimating, in each pixel, at least two equivalent thicknesses respectively associated with at least two basic materials;
wherein the method comprises, following step d), the following steps:
 e) from the equivalent thicknesses resulting from step d), calculating a structural parameter of the object in various pixels,
 f) spatially smoothing the structural parameter calculated in a plurality of pixels, so as to associate, with each pixel, a smoothed structural parameter;
 g) from the structural parameter smoothed in each pixel, and from each spectrum formed in step c), estimating, in each pixel, regularized equivalent thicknesses respectively associated with each basic material;
 h) characterizing the object from the regularized equivalent thicknesses estimated in step g).

With each pixel is associated one portion of the object, said portion being seen by the pixel, i.e. being placed in a solid angle in which the pixel sees the object. By structural parameter of the object in a pixel, what is meant is a structural parameter of that portion of the object which is associated with the pixel. Likewise, by equivalent thickness in a pixel, what is meant is the equivalent thickness of that portion of the object which is associated with the pixel.

According to one embodiment, step d) and/or step g) comprise(s), for each pixel, taking into account calibration spectra, each calibration spectrum being associated with a thickness of each basic material. Step d) and/or step g) may also comprise, for each pixel:

calculating a likelihood function from the spectrum measured by the pixel in c) and from the calibration spectra, each calibration spectrum being associated with at least one calibration material of a known thickness;

determining an equivalent thickness of each calibration material maximizing the likelihood function, each calibration material forming a basic material.

A calibration spectrum may be a spectrum measured or modelled by replacing the object with a calibration object, the calibration object being formed from a thickness of at least one calibration material. The method assumes recourse is made to various calibration spectra, respectively corresponding to different thicknesses of at least two different calibration materials. The calibration materials may correspond to the basic materials.

Steps d) and g) may comprise a step of changing basis, between a start basis, formed by the calibration materials, and an end basis, formed by the basic materials representative of the object, or considered to be representative of the object, so as to obtain an equivalent thickness of each material of the end basis. Thus, from equivalent thicknesses of each calibration material, forming the start basis, an equivalent thickness of each material forming the end basis is obtained. The materials forming the end basis may for example be physiological materials, for example a tissue, or a certain type of tissue, or bone. The change of basis may be established by taking into account a change of basis matrix.

Step d) may comprise:

grouping adjacent pixels together, in order to form a group of pixels;

associating, with each group of pixels, a group spectrum, combining the spectra formed for each pixel of the group of pixels;

such that d) is implemented, for at least one pixel of a group of pixels, from the grouped spectrum associated with the group of pixels.

In step e), for each pixel, the structural parameter may be a thickness of that portion of the object which is associated with the pixel.

In step e), for each pixel, the structural parameter may also represent a composition of that portion of the object which is associated with the pixel. In this case, the structural parameter, determined in each pixel, may:

be an effective atomic number, determined from the equivalent thicknesses estimated in d);

or comprises a ratio between an equivalent thickness of a basic material and the sum of the equivalent thicknesses estimated in d).

Step h) may comprise a characterization of the various portions of the object respectively associated with various pixels. The characterization may comprise:

forming an image showing the regularized equivalent thickness of a basic material;

and/or determining an effective atomic number from the regularized equivalent thicknesses of each basic material;

and/or a ratio between a regularized equivalent thickness of a basic material and the sum of the regularized equivalent thicknesses of each basic material.

In step b), the detector may be moved with respect to the object or the object may be moved with respect to the detector. The radiation source may be moved with respect to the object or with respect to the detector.

A second subject of the invention is a device for characterizing an object, comprising:

a radiation source, configured to emit ionizing electromagnetic radiation;

a holder, intended to receive an object, such that the object is placed between the radiation source and the detector;

a detector, comprising pixels, the detector being configured to detect ionizing electromagnetic radiation and to form, in a plurality of pixels, a spectrum of the detected radiation;

a processor, configured to receive the spectra formed by the detector and to implement d) to h) of a method according to the first subject of the invention.

Other advantages and features will become more clearly apparent from the following description of particular embodiments of the invention, which embodiments are given by way of nonlimiting example, and shown in the figures listed below.

FIGURES

Figure 2:
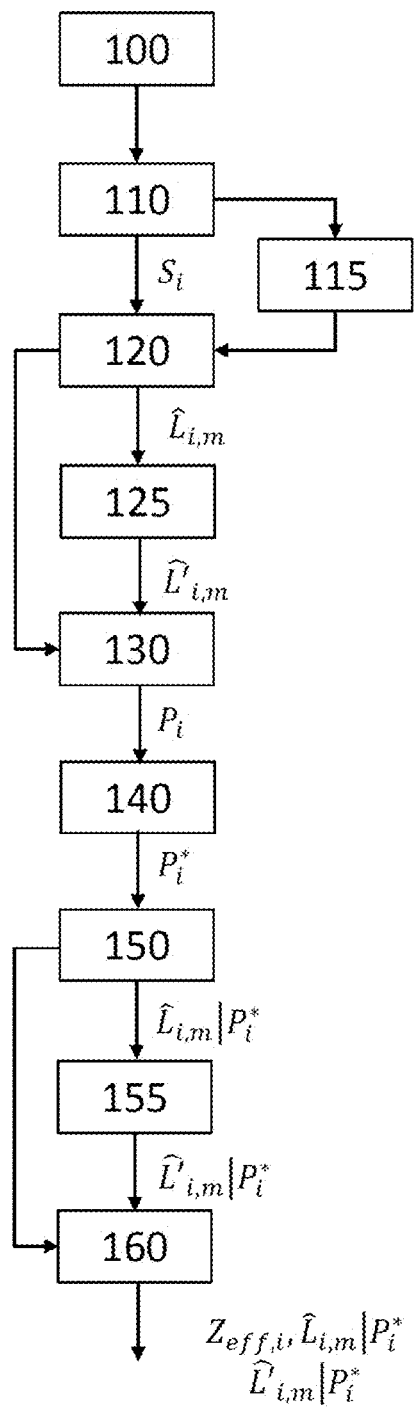
FIG. 2 shows the main steps of a method according to the invention.
Figure 3E:
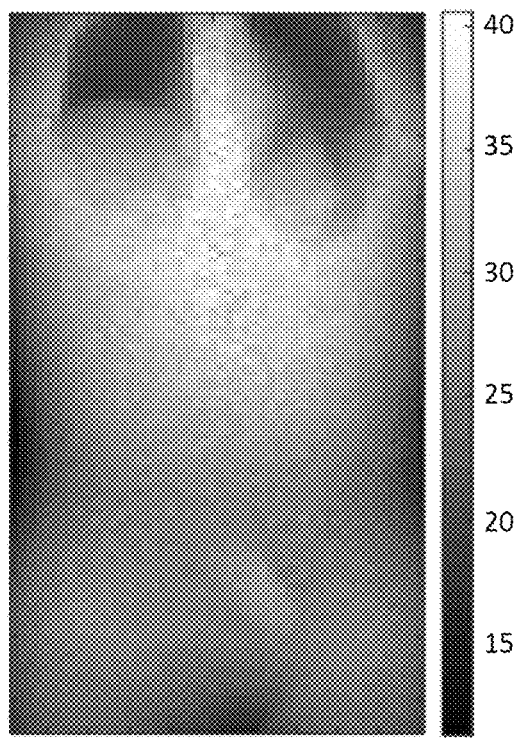
Figure 3F:
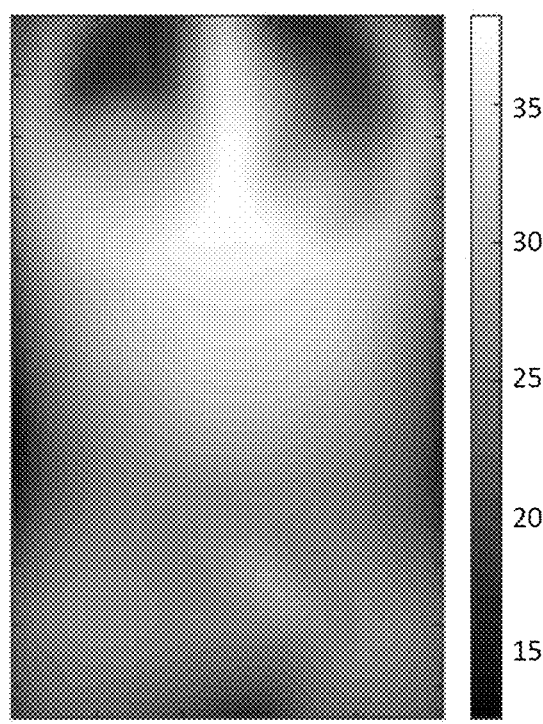
Figures 3G, 3H:
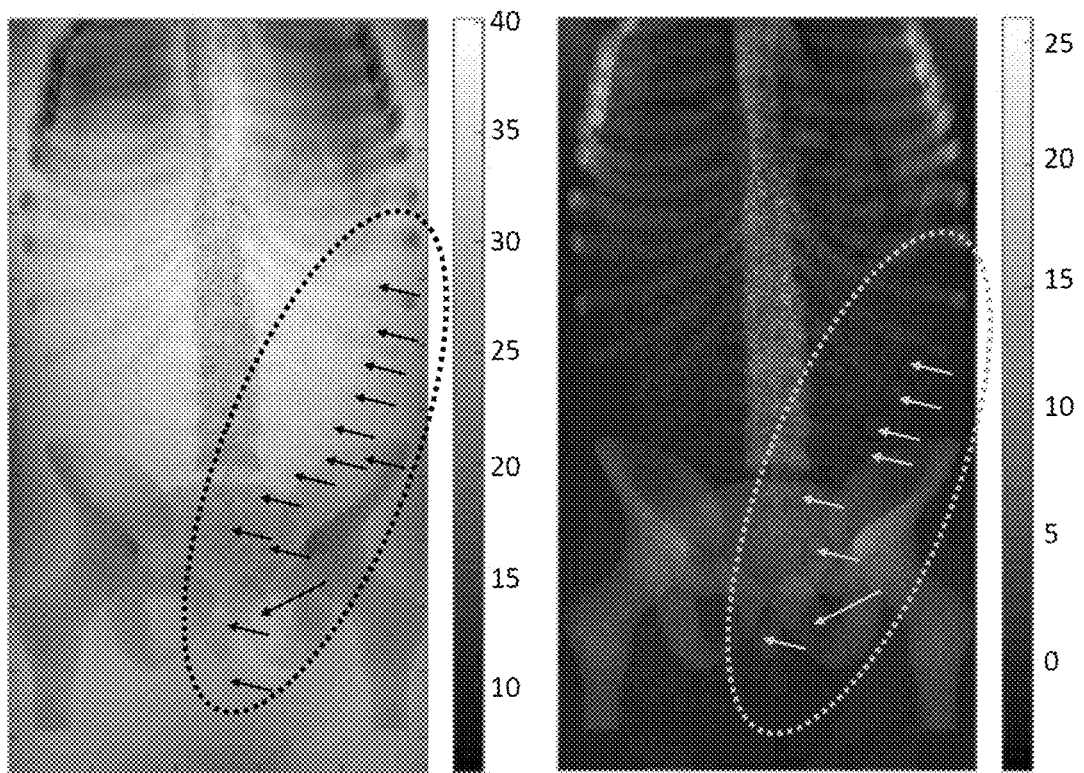

FIGS. 3A to 3H are simulated images of a phantom, which illustrate the implementation of the method described with reference to FIG. 2. FIG. 3A is a radiograph of the phantom used. FIG. 3B shows a simulation of the number of photons incident on the pixels of the detector during the trial. FIGS. 3C and 3D respectively show the spatial distributions of the equivalent thickness of bone and of the equivalent thickness of tissue corresponding to the phantom shown in FIG. 3A. FIG. 3E shows a spatial distribution of a structural parameter obtained from the equivalent thicknesses of bone and of tissue respectively illustrated in FIGS. 3C and 3D. In the example shown in FIG. 3E, the parameter in question is the thickness of the object. FIG. 3F shows a spatial smoothing of the parameter mentioned with reference to FIG. 3E. FIGS. 3G and 3H respectively show the spatial distributions of the equivalent thickness of bone and of the equivalent thickness of tissue of the phantom, these equivalent thicknesses having been calculated taking into account the smoothed parameter shown in FIG. 3E.

Figures 3I, 3J:
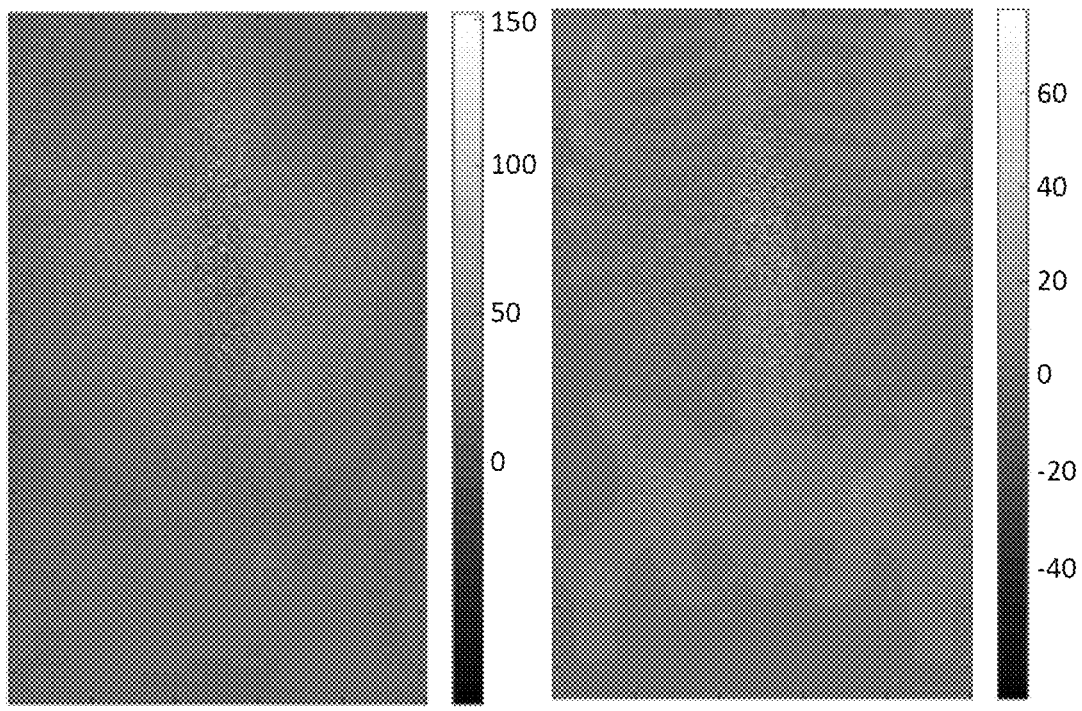

FIGS. 3I and 3J respectively show the spatial distributions of the equivalent thickness of bone and of the equivalent thickness of tissue of the phantom, these equivalent thicknesses having been calculated using a prior-art method.

Figure 4A:
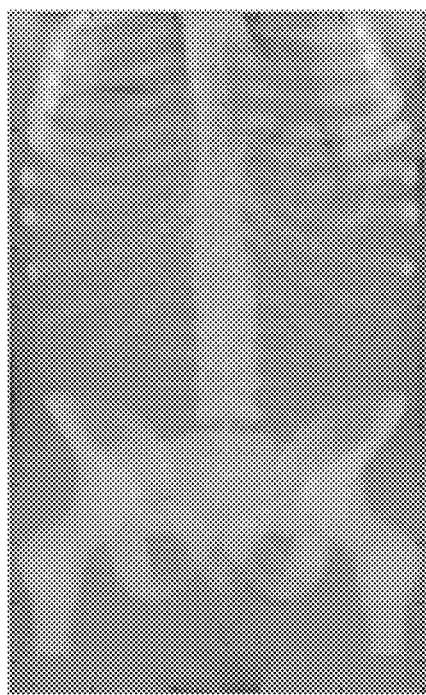
Figure 4B:
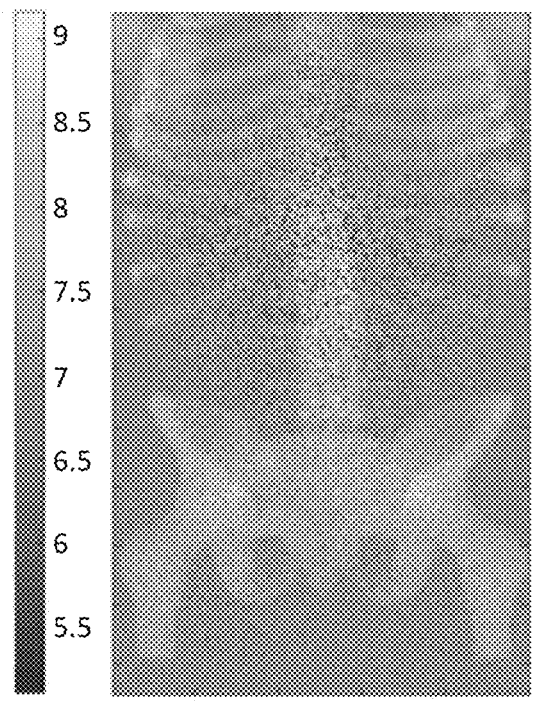

FIGS. 4A and 4B show a spatial distribution of the effective atomic number of the phantom.

FIGS. 4A and 4B were respectively obtained implementing and without implementing the invention.

Figure 5A:
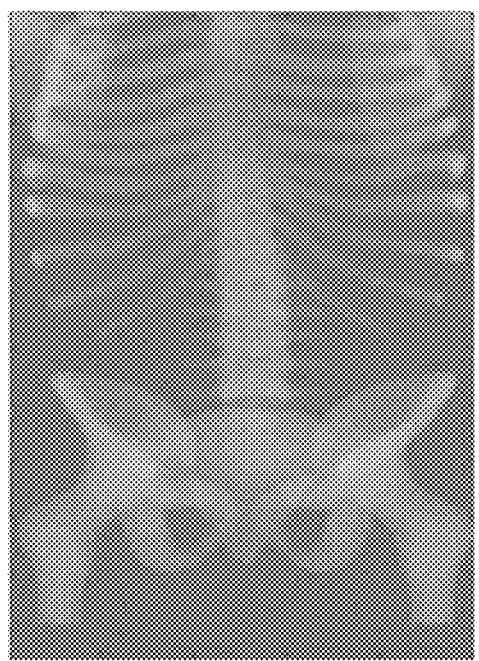
Figure 5B:
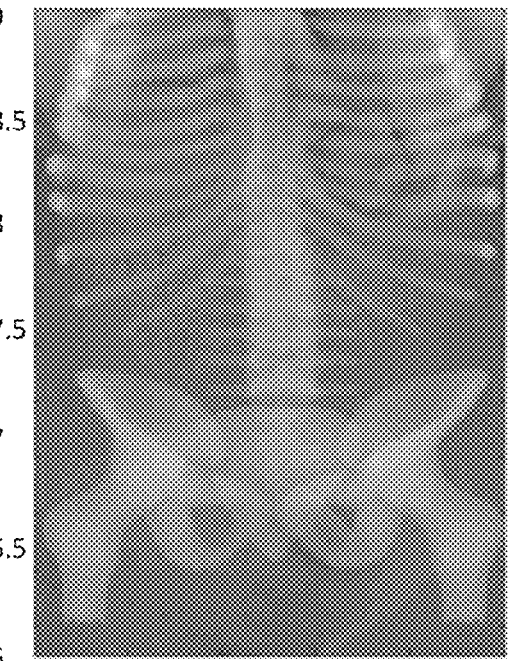
Figure 5C:
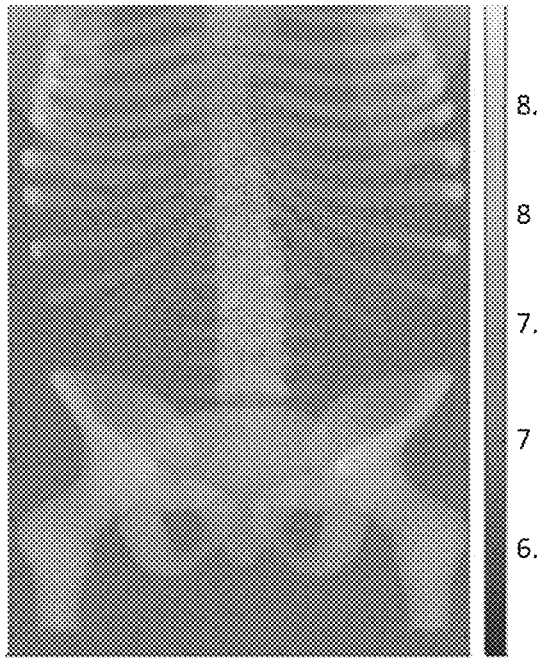

FIGS. 5A, 5B and 5C show a spatial distribution of an effective atomic number of the phantom. FIGS. 5A and 5C were obtained without implementing the invention, the number of incident photons per pixel respectively being $10^6$ and $10^5$.

FIG. 5B was obtained by implementing the invention, the number of incident photons per pixel being $10^5$.

DESCRIPTION OF PARTICULAR EMBODIMENTS

Figure 1:
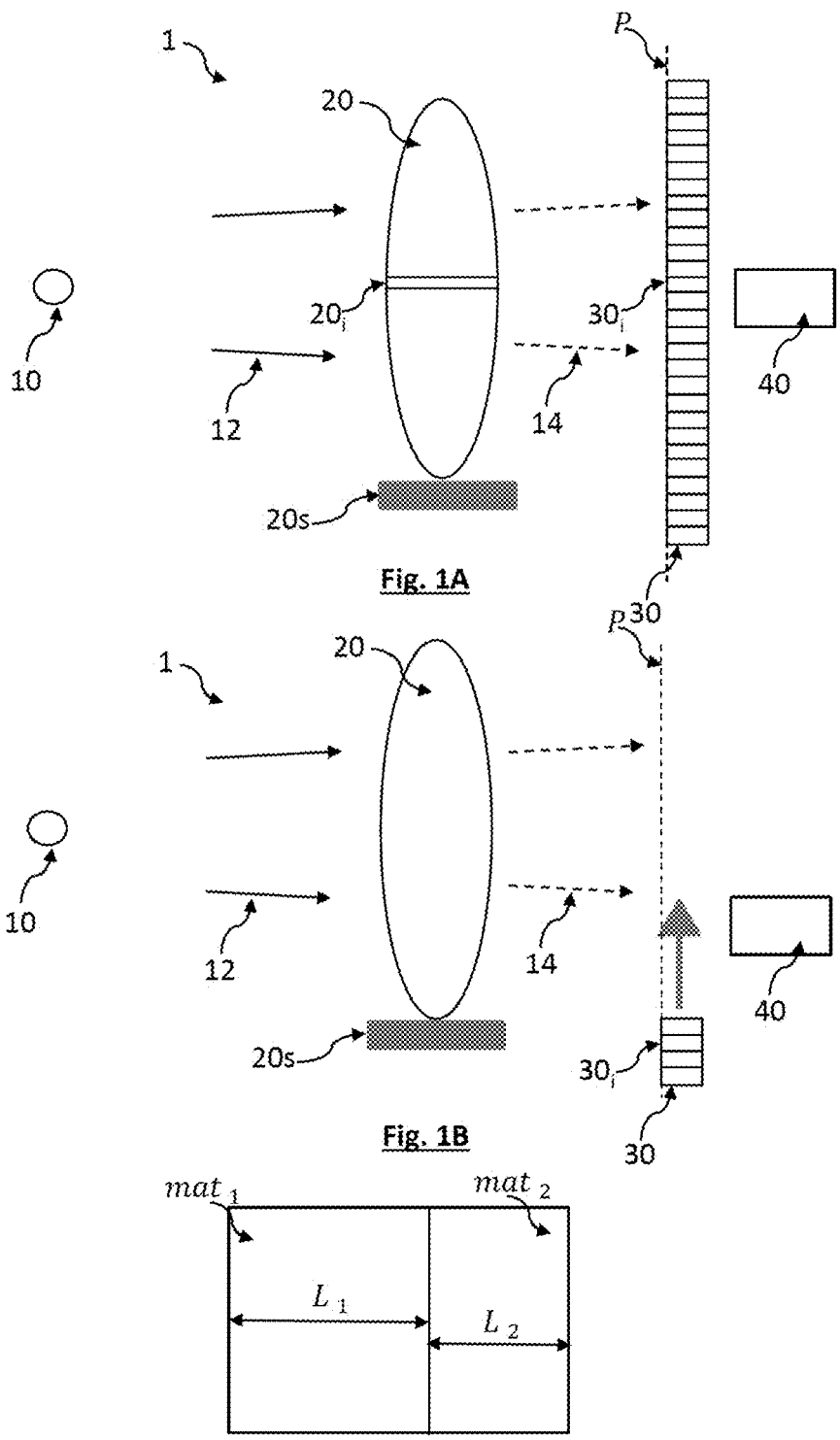
FIGS. 1A and 1B show two examples of devices allowing the invention to be implemented.
FIG. 1C shows an example of a calibration object able to be used to calibrate the method implemented in the invention.

FIGS. 1A and 1B show devices 1 for characterizing an object 20, allowing the invention to be implemented. In each of these figures, the device 1 comprises a radiation source 10 and a detector 30. It also comprises a holder 20s, configured to receive an object, such that when the object 20 is placed on the holder 20s, it is interposed between the radiation source 10 and the detector 30.

The radiation source 10 is configured to emit ionizing electromagnetic radiation 12, called the incident radiation, toward the object 20, the latter being interposed between the radiation source 10 and the detector 30. The detector 30 may comprise elementary detectors $30_i$ taking the form of pixels $30_i$ arranged in a plane, called the detection plane P. The index i designates the coordinates of each pixel in the detection plane. The pixels may be arranged in a line but in general, they are arranged in a two-dimensional regular matrix array.

The object 20 may be a living biological tissue, for example one portion of the body of an animal or a human being. The device 1 is then a medical imaging device or a walk-through airport security detector. The object may also be an industrial part or a piece of luggage, the device then being used for the purposes of nondestructive testing or inspection. In the example that follows, the device 1 is a walk-through airport security detector, intended to detect the presence of illicit substances.

The term ionizing electromagnetic radiation designates electromagnetic radiation consisting of photons of energy higher than 1 keV, and preferably lower than 5 MeV. The energy range of the ionizing radiation may be comprised between 1 keV and 2 MeV, but it most often lies between 1 keV and 150 keV or 300 keV. The ionizing radiation may be X-ray or γ radiation. Preferably, the radiation source 10 is polyenergetic, the incident radiation being emitted in an energy range generally extending over several tens or even hundred keV. It is notably a question of an x-ray tube.

The object 20 irradiated by the source 10 transmits, to the detector 30, radiation 14, called transmitted radiation, or attenuated radiation, the latter reaching the pixels $30_i$. Each pixel $30_i$ is an elementary spectrometric detector comprising:
- a detector material, able to interact with the photons of the radiation 14 transmitted by the object, this material being of scintillator type or, preferably, a semiconductor material compatible with a use at room temperature, of CdTe or CdZnTe type;
- an electronic circuit, able to generate a signal the amplitude of which depends, and is preferably proportional to, the energy deposited by each photon interacting in the detector material;
- a spectrometry circuit, able to establish an energy spectrum, denoted $S_i$, of the signals detected during a time period, called the acquisition period.

The characterizing device 1 also comprises a processing unit 40 allowing the processing operations described below to be implemented. The processing unit 40 may comprise a microprocessor and/or electronic microcontrollers.

Under the effect of the irradiation by the incident radiation 12, the object 20 transmits radiation 14, called transmitted radiation, to the detector 30. Each pixel $30_i$ forms an energy spectrum $S_i$ of the transmitted radiation 14.

The term energy spectrum $S_i$ corresponds to a histogram of the amplitude of the signals detected in the acquisition period of the spectrum. A relationship between the amplitude A and the energy E may be obtained via an energy calibration function g such that E=g (A), according to principles known to those skilled in the art. An energy spectrum $S_i$ is therefore a vector, each term $S_i(k)$ of which represents an amount of radiation detected by the pixel $30_i$ in an energy range $E_k \pm \delta E/2$, with $\delta E$ being the spectral width of each channel k. k designates the rank of the channel, with $1 < k \leq K$, K designating the number of channels of the spectrum.

FIG. 1B shows a detector 30 that is movable with respect to the object 20. During an irradiation of the object 20, the detector is moved with respect to the object 20, and acquires spectra of the radiation 14 transmitted by the object 20. The movement of the detector 30 is indicated by an arrow. Such a configuration allows a detector with a small number of pixels to be used. However, it requires the detector 30 to be moved with respect to the object in order to increase the field of view. Alternatively, the object 20 may move between the radiation source 10 and the detector 30.

Thus, whatever the embodiment, during the irradiation of the object 20, spectra are acquired in various pixels $30_i$, each pixel $30_i$ corresponding to one portion $20_i$ of the object, which portion is associated with the pixel. Thus, a spectral image of the object, each pixel of which is a spectrum of radiation transmitted by that portion $20_i$ of the object 20 which is associated with the pixel $30_i$, is obtained. By that portion $20_i$ of the object which is associated with the pixel $30_i$, what is meant is that portion, of the object, which is seen by the pixel, i.e. that portion which is located in a field of view of the pixel, and therefore placed in a solid angle in which the pixel $30_i$ sees the object 20. That portion $20_i$ of the object which is associated with a pixel $30_i$ is generally located in alignment between the radiation source 10 and the pixel $30_i$.

The object 20 may be replaced by a calibration object, composed of one or more basic materials, the nature and thickness of which are known. Such a calibration object is shown in FIG. 1C. In this example, a calibration object comprising a first basic material mat1 of thickness $L_1$ and a second basic material mat2 of thickness $L_2$ have been shown. The basic materials are materials that are accessible and easily machinable, so as to be able to provide various calibration objects, in which the thickness of each basic material is variable. A basic material may for example be PVC (polyvinyl chloride), or polyethylene, or polypropylene. The calibration of the method described above below consists in providing various calibration objects, so as to obtain calibration spectra $S_{cal}(L_1,L_2)$, by making and $L_1$ and $L_2$ vary. Each calibration spectrum $S_{cal}$ is a one-dimensional vector (K,1), where K represents the number of channels of a spectrum.

The calibration spectra together form a calibration base. The calibration base may be completed by interpolations so as to take into account thicknesses of basic materials not available in the calibration of objects.

The main steps of a method for characterizing an object 20 will now be described with reference to FIG. 2 and FIGS. 3A to 3H.

Step 100: irradiating the object. The object 20 is irradiated by the radiation source 10.

Step 110: acquiring spectra $S_i$ of the radiation transmitted by the object 30, with various pixels $30_i$ of the detector 30. Each pixel $30_i$ is associated with one portion $20_i$ of the object. Two different pixels are respectively associated with two different portions of the object 20.

Step 115: grouping pixels. This step is optional. With each pixel $30_i$ is associated a group of pixels $G_j$. The group of pixels $G_j$ with which the pixel $30_i$ is associated is formed by pixels adjacent to the pixel $30_i$. When the detector is a two-dimensional matrix array of pixels, it is possible to form J groups of pixels $G_j$. Each group of pixels for example comprises 5×5 pixels, or 10×10 pixels. The spectra $S_i$ acquired by the pixels of a given group of pixels $G_j$ may be added, so as to form a spectrum $S_j$ representative of the group of pixels. This operation corresponds to a binning operation. This allows a spectrum $S_j$ having a better signal-to-noise ratio than the spectrum $S_i$ formed by each elementary pixel to be formed. In contrast, spatial resolution is degraded. At the end of this step, the spectrum $S_i$ associated with each pixel $30_i$ of a given group of pixels $G_j$ is replaced by the spectrum $S_j$ established for the group of pixels $G_j$.

Step 120: decomposing the attenuation into a basis of materials.

This step comprises a decomposition of the attenuation $att_i$ into a basis of calibration materials. As explained with reference to expression (1), this amounts to estimating, for each pixel $30_i$, a pair of equivalent thicknesses $(\hat{L}_{i,1}, \hat{L}_{i,2})$, such that:

$$att_i \approx \hat{L}_{i,1}\mu_1 + \hat{L}_{i,2}\mu_2 \quad (2).$$

More generally, when the spectra $S_i$ are defined in K channels, K being an integer higher than or equal to 2, the attenuation may be decomposed into a number M of thicknesses, $\hat{L}_{i,m=1} \ldots \hat{L}_{i,m=M}$, called equivalent thicknesses, of M different calibration materials, with M≤K. M designates the number of calibration materials in question. The method then comprises estimating M equivalent thicknesses $\hat{L}_{i,m}$ with $att_i \approx \sum_{m=1}^{M} \hat{L}_{i,m}\mu_m$ (3) where $\mu_m$ is a linear attenuation spectral function of the calibration material $mat_m$.

When a spectrum $S_j$ is acquired with identical acquisition parameters to each calibration spectrum $S_{cal}$, the equivalent thicknesses corresponding to the acquired spectrum $S_i$ may be obtained by identifying the spectrum of the calibration base closest to the acquired spectrum. By identical acquisition parameters, what is meant is: same radiation source, same detector, same acquisition duration, same distances between the radiation source and the object and between the object and the detector.

The equivalent thicknesses may be estimated using the method described in document EP3106864, and more precisely between paragraphs [0060] and [0081] of this document. If $S_{cal}(L_1 \ldots L_M)$ designates a spectrum of the calibration base, obtained using a calibration object comprising respectively thicknesses $L_1 \ldots L_M$ of basic materials $mat_1 \ldots mat_M$, it is possible to define, for each spectrum $S_i$, a likelihood function $V_i$ such that:

$$\ln(V_i(S_i, S_{cal}(L_1 \ldots L_M))) = (-\sum_{k=1}^{K} S_{cal}(L_1 \ldots L_M) + \sum_{k=1}^{K} (S_i \times \ln(S_{cal}(L_1 \ldots L_M)))) \quad (4)$$

The equivalent thicknesses $\hat{L}_{i,m=1} \ldots \hat{L}_{i,m} \ldots \hat{L}_{i,m=M}$ corresponding to the spectrum $S_i$ measured by each pixel $30_i$ are those maximizing the likelihood function. Thus, $$\hat{L}_{i,m=1} \ldots \hat{L}_{i,m=M} = \mathrm{argmax}(\ln(V_i(S_i, S_{cal}(L_1 \ldots L_M)))) \quad (5)$$

and $$-\ln\left(\frac{S}{S_0}\right) = att_i \approx \sum_{m=1}^{M} \hat{L}_{i,m}\mu_m \quad (6)$$

$S_0$ being a spectrum of the radiation detected by the detector 30 in the absence of an object placed between the radiation source 10 and the detector 30.

According to expression (6), the attenuation $att_i$ corresponding to the spectrum $Sp_i$ measured by each pixel $30_i$ may be decomposed into a basis of calibration materials $mat_1 \ldots mat_M$, the attenuation being able to be likened to a sum of the linear attenuations of each material of the calibration base, weighted by the equivalent thicknesses respectively associated with each basic material.

Step 125 Changing basis.

The equivalent thicknesses established in step 120 are respectively associated with basic materials $mat_1 \ldots mat_M$ used in the calibration, i.e. with calibration materials. The basic materials used during the calibration form a start basis. It is possible to carry out a change of basis, so that the spectrum is expressed as a function of basic materials from which the object is liable to be composed. For example, when the analyzed object is a body of an animal or an individual, the basic materials may be materials $mat'_1 \ldots mat'_M$ representative of physiological elements, for example bone or tissues. The equivalent thicknesses $\hat{L}_{i,m=1} \ldots \hat{L}_{i,m} \ldots \hat{L}_{i,m=M}$ expressed in the start basis $mat_1 \ldots mat_m \ldots mat_M$ may be expressed in an end basis $mat'_1 \ldots mat'_m \ldots mat'_M$. The change of basis is obtained via:

$$\begin{bmatrix} \hat{L}'_{i,m=1} \\ \vdots \\ \hat{L}'_{i,m=M} \end{bmatrix} = T \begin{bmatrix} \hat{L}_{i,m=1} \\ \vdots \\ \hat{L}_{i,m=M} \end{bmatrix} \quad (7)$$

where $\hat{L}'_{i,m=1} \ldots \hat{L}'_{i,m} \ldots \hat{L}'_{i,m=M}$ are the equivalent thicknesses in the end basis $mat'_1 \ldots mat'_m \ldots mat'_M$ and T is a change of basis matrix, of (M,M) size.

The matrix T may be obtained knowing the linear attenuation spectral functions of each basic material. Let Y be a matrix of the linear attenuation spectral functions of the start basic materials $mat_1 \ldots mat_M$, and Z a matrix of the linear attenuation spectral functions of the materials of the end basis $mat'_1 \ldots mat'_M$.

$$Y = \begin{bmatrix} \mu_{mat_1}(E_1) & \cdots & \mu_{mat_M}(E_1) \\ \vdots & \ddots & \vdots \\ \mu_{mat_1}(E_K) & \cdots & \mu_{mat_M}(E_K) \end{bmatrix} \quad (8)$$

$$\text{and } Z = \begin{bmatrix} \mu_{mat'_1}(E_1) & \cdots & \mu_{mat'_M}(E_1) \\ \vdots & \ddots & \vdots \\ \mu_{mat'_1}(E_K) & \cdots & \mu_{mat'_M}(E_M) \end{bmatrix} \quad Y = Z.T$$

Y and Z are matrices of (K,M) size and T is a change of basis matrix of (M,M) size and . designates the matrix product.

The change of basis matrix T may be determined via a method of the least squares type, such that: $T = Z^* \cdot Y$ (9) where $Z^*$ is the pseudo inverse of Z: $Z^* = (Z^t \cdot Z)^{-1} \cdot Z^t$ (10) and where t designates the transpose operator.

From a start basis, composed of the materials polypropylene and PVC, it is possible to express the equivalent thicknesses in an end basis composed of soft tissues and bone, by implementing equation (8) and using a change of basis matrix T such that:

$$T = \begin{pmatrix} 1.11 & -0.97 \\ -0.09 & 1.55 \end{pmatrix}$$

Step 125 is optional. The following steps may be implemented using the equivalent thicknesses in the start basis, i.e. in the basis formed by the calibration materials, or in the end basis, comprising materials different from the calibration materials, and which are more representative of the observed object.

An implementation of steps 100 to 125 has been simulated using a phantom simulating a thorax and an abdomen of an individual, into which capsules of narcotics were inserted. The simulated capsules contained pure cocaine ($C_{17}H_{21}NO_4$) mixed with an adulterant ($C_{11}H_{12}N_2S$). The fractions by weight of pure cocaine and of adulterant were 50% and 50%. The targeted application was the detection of the presence of narcotics carried by an individual, via an inspection of the type carried out with a walk-through airport security detector. FIG. 3A shows a simulated radiograph of the phantom. Irradiation of the phantom with a radiation source consisting of an x-ray generator raised to a potential of 160 kV was simulated. The radiation source 10 was coupled to an aluminum filter of 2 mm thickness, so as to filter low-energy photons. In the absence of object 20, the number of photons reaching each pixel was equal to 6000. The spectra acquired with a CdTe sensor of 3 mm thickness, forming a matrix array of 500×1152 pixels was simulated, the exposed area of each pixel being 0.8×0.8 mm. Each spectrum comprised 64 energy channels. FIG. 3B shows the average number of photons received by each pixel.

For each pixel $30_i$, the spectrum $S_i$ of the radiation 14 attenuated by the object was simulated. The spectrum $S_i$ was representative of the attenuation $att_i$ of a portion $20_i$ of the object, which portion was associated with one pixel. Each pixel $30_i$ was grouped with others so as to form groups of 10×10 pixels. The spectrum $S_i$ of each pixel was replaced by a sum of the spectra of the groups of pixels comprising said pixel. The attenuation $att_i$ corresponding to each spectrum $S_i$ was then decomposed using a basis of calibration materials formed from PVC and from polypropylene, so as to estimate equivalent thicknesses $\hat{L}_{i,1}, \hat{L}_{i,2}$ for each pixel $30_i$. A change of basis was then carried out, so as to obtain the equivalent thicknesses $\hat{L}'_{i,1}, \hat{L}'_{i,2}$ of tissue and of bone. FIGS. 3C and 3D respectively show the equivalent thicknesses $\hat{L}'_{i,1}, \hat{L}'_{i,2}$ of tissue and bone obtained from these spectra. In these figures, the greyscale corresponds to thicknesses expressed in cm.

Step 130. Calculating a structural parameter of the object.

In this step, the equivalent thicknesses resulting from step 120 or step 125 are combined, in each pixel, so as to calculate, in each pixel $30_i$, a structural parameter $P_i$ of the object. More precisely, it is a question of combining the thicknesses $\hat{L}_{i,1} \ldots \hat{L}_{i,m} \ldots \hat{L}_{i,M}, \hat{L}'_{i,1} \ldots \hat{L}'_{i,m} \ldots \hat{L}'_{i,M}$, determined in each pixel $30_i$, in order to calculate a structural parameter of that portion of the object $20_i$ which is associated with the pixel.

The structural parameter $P_i$ may be a dimension of the object, for example a thickness, or a composition of the object. The structural parameter $P_i$ is a function $f$ of the thicknesses determined beforehand. Thus, $P_i = f(\hat{L}_{i,1} \ldots \hat{L}_{i,M})$ (11) or $P_i = f(\hat{L}'_{i,1} \ldots \hat{L}'_{i,M})$ (11').

In a first example, the structural parameter is a thickness of the object. In this example, the parameter $P_i$ calculated, in each pixel $30_i$, is a sum of the thicknesses resulting from step 120 or 125. For example, $P_i = \sum_{m=1}^{m=M} \hat{L}_{i,m}$ (12) where $P_i = \sum_{m=1}^{m=M} \hat{L}'_{i,m}$ (12'). In this example, the parameter $P_i$ is the thickness of that portion $20_i$ of the object which is associated with the pixel $30_i$. FIG. 3E shows an embodiment of this example, based on the obtained thicknesses of tissue $\hat{L}'_{i,1}$ and of bone $\hat{L}'_{i,2}$, for each pixel $30_i$. In FIG. 3E, the greyscale corresponds to the value of the structural parameter in each pixel, i.e. the thickness of the object calculated at each pixel. The latter corresponds to the thickness of that portion $20_i$ of the object which is associated with each pixel $30_i$.

At the end of step 130, a spatial mesh of the structural parameter $P_i$ is achieved, the latter being calculated for each pixel and for each group of pixels.

Step 140: spatially smoothing the structural parameter of the object

In this step, the structural parameter $P_i$ of the object, determined in each pixel in step 130, undergoes spatial smoothing. The underlying idea is that the structure of the examined object does not undergo abrupt variations, and that two parameters determined respectively for two adjacent pixels, i.e. for two adjacent portions of the object, will not vary discontinuously. Such an assumption is particularly relevant when the structural parameter is the thickness of the object, the object being a part of an animal or an individual. Step 140 is a spatial smoothing of the mesh of the structural parameter $P_i$ resulting from step 130, so as to obtain, for each pixel, a smoothed structural parameter $P_i^*$. Such spatial smoothing may be carried out by implementing smoothing filters known to those skilled in the art, for example a Gaussian filter, a median filter or a Savitzky-Golay filter. FIG. 3F shows spatial smoothing of Savitzky-Golay type carried out on the spatial mesh of the structural parameter $P_i$ shown in FIG. 3E. In this example, the Savitzky-Golay filter was applied in a window of 11 pixels using a polynomial of degree 7. In FIG. 3F, the greyscale corresponds to the value of the smoothed parameter $P_i^*$ in each pixel, i.e. the thickness of the object, at each pixel, after spatial smoothing. This step may comprise a spatial interpolation, in particular when the structural parameter is established only for certain pixels that are distant from one another.

At the end of step 140, a spatial mesh of a smoothed structural parameter $P_i$ is obtained, the latter being calculated for each pixel $30_i$, i.e. for each portion $20_i$ of the object respectively associated with one pixel.

Step 150: decomposing a second time into a basis of materials.

This step is similar to step 120. However, whereas step 120 is implemented without a priori, step 150 is carried out using the value of the smoothed structural parameter $P_i^*$ determined in each pixel. In step 150, the equivalent thicknesses $\hat{L}_{i,m=1}|P_i^* \ldots \hat{L}_{i,m}|P_i^* \ldots \hat{L}_{i,m=M}|P_i^*$ corresponding to the spectrum $S_i$ are determined, as described with reference to step 120. However, and this is an important element of the invention, the value, for each pixel $30_i$, of the smoothed structural parameter $P_i^*$, is taken into account, said value relating the corresponding equivalent thicknesses $\hat{L}_{i,m=1}|P_i^* \ldots \hat{L}_{i,m}|P_i^* \ldots \hat{L}_{i,m=M}|P_i^*$ to the pixel in question. The notation $\hat{L}_{i,m}|P_i^*$ designates an equivalent thickness $\hat{L}_{i,m}$ knowing the smoothed structural parameter. When the structural parameter in question is the thickness of the object, the equivalent thicknesses $\hat{L}_{i,m=1}|P_i^* \ldots \hat{L}_{i,m}|P_i^* \ldots \hat{L}_{i,m=M}|P_i^*$ are each estimated knowing that $\sum_{m=1}^{m=M} \hat{L}_{i,m} = P_i^*$. It is therefore a question of a constrained estimation, the estimated quantities being such that $f(\hat{L}_{i,1} \ldots \hat{L}_{i,M}) = P_i^*$.

When the equivalent thicknesses are estimated by maximizing a likelihood function, expression (5) is replaced by:

$$\hat{L}_{i,m=1}|P_i^* \ldots \hat{L}_{i,m=M}|P_i^* = \mathrm{argmax}(\ln(V_i(S_i, S_{cal}(L_1 \ldots L_M))) - \lambda g(f(L_1 \ldots L_M), P_i^*)) \quad (15)$$

where:
- $g(f(L_1 \ldots L_M), P_i^*)$ is a regularization function, taking into account the function $f$ described in expression (11) and the value of the smoothed parameter $P_i^*$ at the pixel $30_i$ in question. In a first example, $g(L_1 \ldots L_M, P_i^*)$ requires $P_i^* = f(L_1 \ldots L_M)$. In another example, the constraint exerted by the regularization function g is less. The regularization function g may be a probability law applied to $f(L_1 \ldots L_M)$, and the average value of which is $P_i^*$. For example, the function g requires $f(L_1 \ldots L_M)$ follow a Gaussian law centred on $P_i^*$, with a predefined standard deviation.
- $\lambda$ is a weighting factor weighting to what extent the regularization function g is taken into account;
- $\hat{L}_{i,m=1}|P_i^* \ldots \hat{L}_{i,m=M}|P_i^*$ are equivalent thicknesses regularized knowing the smoothed parameter $P_i^*$.

At the end of step 150, thicknesses $\hat{L}_{i,m=1}|P_i^* \ldots \hat{L}_{i,m=M}|P_i^*$, which are said to be regularized by the smoothed parameter $P_i^*$, are obtained for each pixel $30_i$. The regularized thicknesses are calculated for each pixel. However, unlike the prior art, because the smoothed parameter $P_i^*$ is taken into account, the regularized thicknesses take into account the structure of the object.

Step 155: changing basis.

From the equivalent thicknesses $\hat{L}_{i,m=1}|P_i^* \ldots \hat{L}_{i,m=M}|P_i^*$ in the basis of the calibration materials, it is possible to obtain equivalent thicknesses $\hat{L}'_{i,m=1}|P_i^* \ldots \hat{L}'_{i,m=M}|P_i^*$ in another basis, by applying expression (8) described with reference to step 125. This step is optional.

FIGS. 3G and 3H respectively show the equivalent thicknesses $\hat{L}'_{i,m=1}|P_i^* \ldots \hat{L}'_{i,m=M}|P_i^*$ of tissue and bone obtained, for each pixel $30_i$, by taking into account the smoothed parameter $P_i^*$. In these figures, the greyscale corresponds to thicknesses expressed in cm.

Step 160: characterizing the object.

From the regularized equivalent thicknesses output from step 150 or step 155, it is possible to characterize the object 20. The characterization may be carried out directly from the equivalent thicknesses $\hat{L}_{i,m=1}|P_i^* \ldots \hat{L}_{i,m=M}|P_i^*$ or $\hat{L}'_{i,m=1}|P_i^* \ldots \hat{L}'_{i,m=M}|P_i^*$.

In the illustrated example, the characterization of the object may be established from FIGS. 3G and 3H. More precisely, in these figures, the presence of suspect shapes, corresponding to the capsules placed in the phantom, are observed. These shapes are located in the abdomen, in a zone encircled by a dashed line. Certain thereof are indicated by an arrow.

FIGS. 3I and 3J are representative of the prior art, and in particular of a method such as described in EP3106864. FIGS. 3G and 3H correspond to an implementation of the invention. Comparison of FIGS. 3G and 3I on the one hand and of FIGS. 3H and 3J on the other hand show the improvement in image quality achieved by the invention. The improvement made is undeniable. The method described above allows capsules to be located while exposing the subject to a low exposure, of about 1 μGy.

Thus, it is possible to characterize the object 20 directly from an image representing regularized equivalent thicknesses, i.e. the thicknesses obtained in step 150 or 155.

From the regularized equivalent thicknesses, it is possible to estimate an effective atomic number of the various portions $20_i$ of the object 20. The effective atomic number $Z_{eff}$ has for example been described in document EP3084406. It is applicable to a chemical compound, and corresponds to a combination of the atomic numbers of the simple bodies from which the compound is formed, each atomic number being assigned a weighting coefficient dependent on the atomic or mass fraction of the simple body in the compound. It is possible to estimate effective atomic number from the regularized equivalent thicknesses, output from step 150 or 155, using the expression:

$$Z_{eff,i} = \left( \frac{\sum_{m=1}^{M} \rho_m \hat{L}_{i,m} | P_i^* Z_{effm}^p}{\sum_{m=1}^{M} \rho_m \hat{L}_{i,m} | P_i^*} \right)^{1/p} \quad (16)$$

where:
- $p = 3$;
- $Z_{effm}$ is the effective atomic number of each basic material $mat_m$; and
- $\rho_m$ is the density of the basic material $mat_m$.

Where:

$$Z_{eff,i} = \left( \frac{\sum_{m=1}^{M} \rho'_m \hat{L}'_{i,m} | P_i^* Z'^{p}_{effm}}{\sum_{m=1}^{M} \rho'_m \hat{L}'_{i,m} | P_i^*} \right)^{1/p} \quad (16')$$

where:
- $p = 3$;
- $Z'_{effm}$ is the effective atomic number of each basic material $mat'_m$; and
- $\rho'_m$ is the density of the basic material $mat'_m$.

FIGS. 4A and 4B are images showing estimations of the effective atomic number of the phantom described above. In FIGS. 4A and 4B, the estimations were carried out by applying expression (16') to equivalent thicknesses output from step 155, implementing the invention, without step 115, and according to the prior art, respectively. It may be seen that FIG. 4A allows certain capsules to be identified. Moreover, the effective atomic number estimated from regularized equivalent thicknesses, obtained by implementing the invention, is less noisy then the effective atomic number estimated from equivalent thicknesses obtained according to the prior art.

FIGS. 5A to 5C are images showing estimations of the effective atomic number of the phantom, without any capsules, the level of irradiation to which the phantom was exposed varying. FIG. 5A was obtained using equivalent thicknesses estimated according to the prior art, the number of incident photons per pixel being $10^6$. FIG. 5B was obtained using regularized equivalent thicknesses estimated by implementing the invention, the number of incident photons per pixel being $10^5$. FIG. 5C was obtained using equivalent thicknesses estimated according to the prior art, the number of incident photons per pixel being $10^5$.

From FIGS. 5A and 5B, it may be seen that the invention allows an image quality equivalent to the prior art to be obtained while decreasing the exposure by a factor of 10. This is particularly important when the analyzed object is a part of an animal or a living individual, because this allows exploitable images to be obtained while decreasing the exposure to ionizing radiation.

From FIGS. 5B and 5C, it may be seen that the invention allows, at constant irradiation level, a higher image quality than the prior art to be obtained.

In the above examples, the structural parameter $P_i$ determined in step 130 and smoothed in step 140 was the thickness of the analyzed object, or more precisely the thickness of the portions $20_i$ of the object respectively associated with each pixel $30_i$.

In another example, the structural parameter $P_i$ relates to the composition of the object. It may be a question of the effective atomic number $Z_{eff,i}$, the latter being obtained from the regularized equivalent thicknesses using expression (16) or (16'). It may also be a question of a relative proportion of one basic material relative to all of the basic materials. For example, the parameter $P_i$ may be a ratio of the regularized equivalent thickness $\hat{L}_{1,i}$ corresponding to the first basic material, to a sum of the regularized equivalent thicknesses corresponding to all of the basic materials $mat_m$. Thus, $$P_i = \frac{\hat{L}_{1,i}}{\sum_{m=1}^{M} \hat{L}_{m,i}}. \qquad (17)$$

Such a parameter may for example be used to rapidly sort objects depending on their composition. One application may be to sorting waste, depending on the presence or absence of additives, or to sorting metal parts. For example, the metal parts may be made of aluminum alloys, which it is desired to sort depending on the presence of particular alloying elements, for example depending on the presence of copper or zinc. In these applications, the presence of particular alloying elements, or additives, leads to a variation in the structural parameter, such as defined by expressions (16), (16') or (17).

The invention allows sorting requiring low irradiation to be carried out, this limiting the duration of the inspection and allowing the rate at which sorting is carried out to be increased.

Whatever the targeted application, the invention allows an object to be characterized while requiring a lower exposure of the latter with respect to the prior art. The invention will possibly be implemented in medical applications, for example for the purpose of assisting with diagnosis, or in applications related to nondestructive testing.

The invention claimed is:

1. A method for characterizing an object, comprising:
   a) placing the object between a radiation source and a radiation detector, the radiation source being configured to emit ionizing electromagnetic radiation that propagates to the object;
   b) irradiating the object with the radiation source and detecting radiation transmitted by the object using the radiation detector, the radiation detector comprising a plurality of pixels, each pixel being associated with one portion of the object;
   c) for each pixel, forming an energy spectrum of the detected radiation, each spectrum comprising at least two distinct energy bands;
   d) from each spectrum formed in c), estimating, in each pixel, at least two equivalent thicknesses respectively associated with at least two basic materials;
   wherein the method comprises, following d):
   e) from the equivalent thicknesses resulting from d), calculating a structural parameter of the object in various pixels, the structural parameter of the object being for each pixel:
      a thickness of that portion of the object which is associated with the pixel;
      or representative of a composition of that portion of the object which is associated with the pixel.
   f) spatially smoothing the structural parameter calculated in a plurality of pixels, so as to associate, with each pixel, a smoothed structural parameter;
   g) from the structural parameter smoothed in each pixel, and from each spectrum formed in c), estimating, in each pixel, regularized equivalent thicknesses respectively associated with each basic material;
   h) characterizing the object from the regularized equivalent thicknesses estimated in g).

2. The method as claimed in claim 1, wherein d) and/or g) comprise(s), for each pixel, taking into account calibration spectra, each calibration spectrum being associated with a thickness of each basic material.

3. The method as claimed in claim 2, wherein d) and/or g) also comprise, for each pixel:
   calculating a likelihood function from the spectrum formed by the pixel in c) and from the calibration spectra, each calibration spectrum being associated with at least one calibration material of a known thickness;
   determining an equivalent thickness of each calibration material maximizing the likelihood function, each calibration material forming a basic material.

4. The method as claimed in claim 3, wherein d) and/or g) comprise(s) a change of basis, between a start basis, formed by the calibration materials, and an end basis, formed by the basic materials representative of the object, so as to obtain an equivalent thickness of each material of the end basis.

5. The method as claimed in claim 1, wherein d) comprises:
   grouping adjacent pixels together, in order to form a group of pixels;
   associating, with each group of pixels, a grouped spectrum, combining the spectra formed for each pixel of the group of pixels;
   such that d) is implemented, for at least one pixel of a group of pixels, from the grouped spectrum associated with the group of pixels.

6. The method as claimed in claim 1, wherein the structural parameter represents a composition of that portion of the object which is associated with each pixel, and wherein the structural parameter, determined in each pixel:
   is an effective atomic number, determined from the equivalent thicknesses estimated in d);
   or comprises a ratio between an equivalent thickness of a basic material and the sum of the equivalent thicknesses estimated in d).

7. The method as claimed in claim 1, wherein h) comprises a characterization of the various portions of the object respectively associated with various pixels.

8. The method as claimed in claim 7, wherein the characterization comprises:
   forming an image showing the regularized equivalent thickness of a basic material;
   and/or determining an effective atomic number from the regularized equivalent thicknesses of each basic material;
   and/or a ratio between a regularized equivalent thickness of a basic material and the sum of the regularized equivalent thicknesses of each basic material.

9. The method as claimed in claim 1, wherein, in b), the detector is moved with respect to the object or the object is moved with respect to the detector.

10. A device for characterizing an object, comprising:
    a radiation source, configured to emit ionizing electromagnetic radiation;
    a holder, intended to receive the object, such that the object is placed between the radiation source and the detector;

a detector, comprising pixels, the detector being configured to detect ionizing electromagnetic radiation and to form, in a plurality of pixels, a spectrum of the detected radiation;

a processor, configured to receive the spectra formed by the detector and to implement d) to h) of a method as claimed in claim 1.

* * * * *